United States Patent [19]

Zenoni et al.

[11] Patent Number: 5,441,874
[45] Date of Patent: Aug. 15, 1995

[54] METHOD FOR THE ACYLATION OF THE 7-AMINO GROUP OF THE CEPHALOSPORANIC RING

[75] Inventors: Maurizio Zenoni, Leffe; Claudio Fuganti, Milan, both of Italy

[73] Assignee: Finpael S.p.A., Milan, Italy

[21] Appl. No.: 86,849

[22] Filed: Jul. 7, 1993

[30] Foreign Application Priority Data

Aug. 7, 1992 [GB] United Kingdom ............ 9216759

[51] Int. Cl.⁶ ............................................. C12P 35/00
[52] U.S. Cl. ......................................... 435/47; 540/222; 540/227; 540/225
[58] Field of Search ............... 540/222, 225; 435/47, 435/50, 51

[56] References Cited

U.S. PATENT DOCUMENTS 3,749,641   7/1973   Takahashi et al.
3,930,949   1/1976   Kutzbach et al.
4,091,245   5/1978   Bouzard et al.
4,517,361   5/1985   Numata et al.
5,292,733   3/1994   Kim et al. ............ 540/227

*Primary Examiner*—Nicholas Rizzo
*Attorney, Agent, or Firm*—Oblon, Spivak, McClelland, Maier & Neustadt

[57] ABSTRACT

A method for the acylation of the 7-amino group of the cephalosporanic ring, according to which a 7-ACA amino thiazolyl protected adduct is prepared by acylating said amino group by an aminothiazolyl acetic acid whose amino group has been protected by a phenyl acetyl or a phenoxy acetyl group, the amino group being then deprotected by aqueous hydrolysis in the presence of penicillin G amidase or respectively penicillin V amidase.

2 Claims, No Drawings

METHOD FOR THE ACYLATION OF THE 7-AMINO GROUP OF THE CEPHALOSPORANIC RING

The present invention relates to a method for the acylation of the 7-amino group of the cephalosporanic ring.

7-ACA (7-amino-3-acetoxymethyl-3-cephem-4-carboxylic acid) of formula

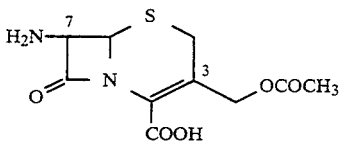

is a well known compound which has been proposed as starting material in various syntheses, in particular in the syntheses of many cephalosporins.

A number of the most important cephalosporins are obtained through the following reaction steps:
a) effecting an acylation of the 7-amino group of the cephalosporanic ring by an optionally substituted aminothiazolyl acetic acid whose amino group has been protected;
b) deprotecting the protected amino group; and
c) optionally substituting the 3-acetoxymethyl group of the cephalosporinic ring by a nucleophilic agent.

The sequencing of the above reported steps can be varied at will. For instance, the step sequencing can be a), b), c); or a), c), b); or c), a), b), too, as it is described in the Journal of Antibiotic, December 1978; 1262–1271 and in the BE-A-823861 by Takeda (concerning the antibiotic CEFOTIAM).

In ever case, the acylation off the 7-amino group of the cephalosporinic ring is carried out with an optionally substituted aminothiazolyl acetic acid whose amino group has been protected, the amino group being then deprotected.

The known protecting groups usable in the practice require the use of expensive starting materials (such as trityl and BOC), critical conditions for introducing the reactants and critical acid conditions for removing the protection.

The creation of the aminothiazol ring directly on the adduct has the shortcoming that it requires the use of highly dangerous reactants such as diketenes and anhydrides.

It has been now surprisingly found that some extremely important advantages are attained if the amino protecting group is a phenyl acetyl group or a phenoxy acetyl group: these protecting groups are cheap, they are easily introduced, and compatible with the carbonyl promoting conditions which are necessary for the reaction with 7-ACA.

The use of phenyl- or phenoxy-acetic acids to protect the amino group of the amino thiazolyl acetic acid (in order to promote the carboxylic group thereof) is extremely important because such a protection provides a very stable adduct extremely difficult to be chemically eliminated, so that said adduct, because of such protection, can be subjected to the subsequent chemical treatments without involving the protecting group.

Further, it has been surprisingly found that the above mentioned protecting groups are selectively removable under extremely mild conditions, by simple hydrolysis in aqueous solution substantially at room temperature in the presence of penicillin G amidase or penicillin V amidase which catalyze the hydrolysis of the amidic bond of the N-phenyl acetyl or N-phenoxy acetyl amino thiazolyl moiety at a much higher speed than the one with which it hydrolyzes the amidic bond that is present in the position 7 of the final compound of the reaction.

The penicillin G amidase and penicillin V amidase enzymes are known per se and their use has been described, for instance, in GB-A-1480850 and GB-A-1473100: by making use of such enzymes it was known to obtain by enzymatic route (in the place of the chemical route) 6-APA starting from pencillin G or penicillin V, and 7-ADCA starting from cephalosporin G or cephalosporin V.

Therefore the use of the N-phenyl- or N-phenoxyacetic protecting group selectively removable by enzymatic hydrolysis in aqueous solution, without either removing the acetic ester group present in the molecule or significantly hydrolyzing the amidic bond in 7, represents a very important economical and ecological advantage with respect to the methods for acylating the 7-amino group of the cephalosporanic ring, in particular for protecting and deprotecting the amino group in the known syntheses of 7-aminothioazolyl cephalosporins.

Of particular important is also the fact that the reaction occurs in an aqueous environment and high yields are obtained.

Consequently, the present invention concerns a method for the acylation of the 7-amino group of the cephalosporanic ring, wherein a 7-ACA amino thiazolyl protected adduct is prepared by acylating said amino group by an optionally substituted aminothiazolyl acetic acid whose amino group has been protected, the protected amino group being thereafter protected, characterized in that the amino protecting group is selected from the group consisting of a phenyl acetyl and respectively of a phenoxy acetyl group and that the deprotection is effected by hydrolysis in aqueous solution at a temperature of from 0° C. to 50° C. and at a pH from 5 to 9 in the presence of an enzyme selected from the group consisting of penicillin G amidase and penicillin V amidase respectively.

In particular, it has been found that said hydrolysis may be effected at a temperature of from 15° C. to 35° C. and at a pH from 6 to 8.

The invention concerns also the novel amino thiazolyl acetic acid and its α-substitution derivatives whose amino group is protected by a phenyl carbonyl group selected from the group consisting of a phenyl acetyl and phenoxy acetyl group; and also the 7-ACA amino thiazolyl protected adduct, where in the protection of the amino group made by a phenyl carbonyl group selected from the group consisting of a phenyl acetyl and phenoxy acetyl group.

Of course, also the novel N-phenylacetyl and N-phenoxyacetyl optionally α-aminothiazolyl acetic acid substituted and 3-substituted cephalosporins form part of the present invention.

In order to make the features of the present invention clear, some non limitative embodiments thereof will now be detailedly described.

The following non limitative examples will illustrate the invention.

EXAMPLE 1

PREPARATION OF THE 7-[2(AMINOTHIAZOL-4-YL)]ACETAMIDO CEPHALOSPORANIC ACID

A) Preparation of N-phenylacetyl amino thiazolyl acetic acid (protected acylating)

18,6 g (0,1 moles) of the ethyl ester of amino thiazolyl acetic acid in 100 ml of organic non hydroxylated solvent (methylene chloride, THF, dioxane, acetonitrile etc.) in the presence of 1,2 molar equivalents of an organic base as triethylamine are added under stirring at 0° to 5° C. with 15,4 g (0,1 moles) off phenyl acetic acid chloride within 15 minutes.

The reaction is complete after some hours at room temperature (TLC on silica in ethyl acetate/hexane 7:3 Rf: about 0,7). The vessel is then cooled under ice, and the organic phase is then washed in sequence with diluted hydrochloric acid, bicarbonate aqueous solution and water. The solution is dried and then evaporated under vacuum. The oily residue solidifies spontaneously. The product can be crystallized by hexane/ethyl aetate. However this is not necessary because the raw product can be used directly for the next step. Said step consists in treating the solution of the above obtained ester with a NaOH aqueous solution, said solution being obtained dissolving 1 g of NaOH every 4 g of ester to be hydrolyzed. A slight heating is produced when the solutions are admixed. The reaction is kept stirred for 5 to 6 hours, a time sufficient to effect hydrolysis, whose development is followed by TLC.

When the reaction is complete, the mixture is evaporated under vacuum to eliminate most of solvent, maintaining the boiling temperature low, so to avoid the amidic bond hydrolysis. The reaction mixture is then diluted with water, under stirring and the cooled and acidified with HCl. The precipitate consisting of the N-phenylacetyl amino thiazolyl acetic acid (hereinafter called compound "X") is collected by filtration and then washed with water on the filter and finally dried giving 22 g (79%).

B) Preparation of the 7-amido-((2-N-phenylacetylamino-4-thiazolyl)-2-acetyl)-3-acetoxymethyl-3-cefem-4-carboxylic acid 13,8 g (0,05 mole of the acid "X" obtained according to A above suspended in 30 ml of methylene chloride are treated with 9,5 g of oxalyl chloride (0,075 mole) and with some drops of DMG at room temperature, under stirring. When the gas development has practically ceased, 3 g further of oxalyl chloride are added, heating under slight reflux for 30 minutes. The reaction is then concentrated under vacuum. The residue, having an intense green colour, is admixed with 50 ml of methylene chloride and is added dropwise, under stirring and under nitrogen atmosphere at −10° C., to a mixture of 12,2 g (0,045 mole) of 7-ACA and 40 ml of triethylamine in 100 ml of methylene chloride.

When the addition is ended, the temperature is allowed to rise to room temperature and then the reaction mixture is washed with cool water and diluted hydrochloric acid.

The dried organic phase is evaporated to give an oily red coloured residue. This material, well dried under vacuum, may solidify spontaneously.

However, if it is admixed with a little volume of ethanol at 50° to 60° C., it permits the separation of a crystalline solid (compounds "Y"), which is collected by filtration. 16,7 g (67%). Similar yields are obtained when treating the 7-ACA suspension in methylene chloride with 2 molar equivalents of BSA, till complete dissolution, followed by the addition of triethylamine and then of the acid chloride.

Alternatively, the same hereabove specified compound can be obtained as follows:

13,8 g (0,05 mole) of the acid obtained according to A above in 300 ml of THF in the presence of 6,2 g (0,06 mole) of N-methyl morpholine are added dropwise with 5,4 g of ethyl cloroformate. After 3 hours, 13,6 g (0,05 mole) of 7-ACA in 50 ml of methylene chloride and 50 ml of triethylamine are added at room temperature.

After 12 hours, always at room temperature, the reaction mixture is concentrated under vacuum, then diluted with methylene chloride and repeatedly washed with diluted HCl and water and finally dried. The reddish residue obtained by evaporating the solvent is then treated with ethanol, thus obtaining a solid 7-ACA amino thiazolyl protected adduct (compound "Y") which is filtered. 14 g (59%).

C) Enzymatic Hydrolysis 5.3 g of the compound "Y" obtained according to B above are suspended in 120 ml of water and the suspension is treated with NaOH 1N at pH 8, at 36° C. All the solid is dissolved within 10–15 minutes. 500 units of the PGA enzyme are then added and the hydrolysis development is followed by HPLC, because no direct correspondence between the consumed base and the hydrolysis evolution is observed. When the starting material has disappeared, the immobilized enzyme is filtered, the reaction mixture is concentrated under vacuum, at a volume of 50 ml, then it is cooled and acidified to pH 3,6. The precipitate is collected and washed off the filter with absolute ethanol. The product is the 7-[2(aminothiazol-4-yl)]acetamido cephalosporanic acid which can be crystallized from aqueous ethanol. 3,3 g (80%).

EXAMPLE 2

Preparation of the 7[((2-amino-4-thiazolyl)acetyl)amino]-3-[[[1-[2-(dimethyl-amino)-ethyl]-1H-tetrazol-5-yl]-thio]methyl-8-oxo-5-thia-1-aza-bicyclo[4,2,0]oct-2-ene-2-carboxylic acid 2HCl (CEFOTIAM)

5 g (12,1 mmoles) of the 7-[2(aminothiazol-4-yl)]acetamido cephalosporanic acid obtained according to Example 1-C above are dissolved in 40 ml of $H_2O$ with 2,3 g (13.2 mmoles) of 1-(2-dimethyl-aminoethyl)-1H-tetrazole-5-thiol (compound "Z") and 2,18 g (26 mmoles) of $NaHCO_3$ at 70° C. The mixture is permitted to react at 70° C. for 2 h following the reaction by TLC.

The mixture is then cooled at 20° C. and the solution, at pH 7, is eluted on XAD 1180.

The product is eluted with a $H_2O$/methanol mixture, evaporating under vacuum the enriched faction and cefotiam is crystallized by adding isopropanol and HCl concentrated. Filtering and drying under vacuum are then effected.

Molar yield: 67%.

Alternatively:

20 mmoles of the 7-[2-(aminothiazol-4-yl)]acetamido cephalosporanic acid of Ex. 1-C are treated with 20 mmoles of the above mentioned compound "Z" in 150 ml di THF/H₂O 1/1 and 40 mmoles of NaHCO₃ at 60° C. under N₂ for 4 hours.

At the end of the reaction, the solution is concentrated under vacuum, adjusting the pit at 7, and extracted for 3 times with 40 ml of CH₂Cl₂. The residual aqueous suspension is further concentrated and acidified at pH 3,0 with concentrated HCl, then it is cooled at 0° C. and filtered. The solid is purified in isopropanol at 50° C. for 30' and then cooled, filtered and dried.

Molar yield: 58%.

EXAMPLE 3

PREPARATION OF CEFOTIAM

A) Preparation of the 7-amino-ceph-3-em-3-1-(2-dimethyl-aminoethyl)-1H-tetrazol-5-thiol-4-carboxylic acid.

15,3 g (88,3 mmoles) of 1-(2-dimethyl-aminoethyl)-1H-tetrazole-5-thiol (compound "Z") are added in 100 ml of trifluoroacetic acid (TFAA) cooled at −5° C. Then 24 g of 7-ACA (88,1 mmoles) are charged, in little amounts, in 30' at a temperature from 0° to −5° C. The disappearing of the 7-ACA is followed by TLC. At the end of reaction, TFAA is evaporated under vacuum at 45° C. 50 ml of THF are added to the concentrate.

The precipitate attained is then filtered under vacuum. The solid is recovered with H₂O at pH 7 and with NaHCO₃ to release the base of the title compound as a white solid which is filtered under vacuum and dried.

Yield: 76%

Alternatively:

15,3 g (88,3 mmoles) of the above mentioned compound "Z" are added in 100 ml of methansulphonic acid cooled at +5° C. 24 g of 7-ACA (88,1 mmoles) are then charged in little amounts at a temperature from 0° to +5° C.

At the end of the reaction, 100 ml of isopropilic acid are added to crystallize the dimethansulphonate salt of the title compound.

Filtering is then effected and the solid is set in 80 ml of H₂O adjusting to pH 7 with NaHCO₃. 30 ml of isopropanol are added and the crystallization of the title compound is effected at 15° C.

Yield: 78%

NMR (δ in DMSO-d6):
2,58 (6H, s, Ndimethyl); 3,22 (2H, t, etero Nmethylen); 3,52 (2H, q AB, 2CH₂); 4,24 (2H, q, 3CH₂); 4,60 (2H,m, CH₂-Ndimethyl); 4,76 (1H, d, 6CH); 4,94 (1H, d, 7CH).

B) Preparation of a N-phenylacetyl protected 3-substituted cephalosporin 10 mmoles of the protected acylating agent "X" in 10 ml of anhydrous DMF and 20 ml of CH₂Cl₂ are treated with 10 mmoles of N-methylmorfoline at −30° C. 10 mmoles of ethyl chloroformate are then added maintaining the temperature at −30° C. for 30'. The mixture is then poured in a 10 mmoles solution of the compound obtained according to A) above, dissolved in 10 ml of DMF, 20 ml of CH₂Cl₂ and 10 mmoles of N methyl morfoline. The condensation reaction is complete after 1 hour; the solvent is evaporated under vacuum and the residual is recovered with a little of water and adjusted to pH 3,5 with concentrated HCl. A crystalline solid is then filtered and purified in isopropanol at 4° C.

The molar yield is 65%.

Alternatively:

20 mmoles of the protected acylating agent "X" are reacted with 20 mmoles of the compound obtained according to A) above, in 200 ml or CH₃CN/H₂O 1/1 and 50 mmoles of NaHCO₃ at 65° C. for 3 hours under N₂ inert atmosphere.

At the end of the reaction, concentration under vacuum is effected, adjusting the pH at 7,0 and then effecting two extractions with 45 ml of CH₂Cl₂. The aqueous suspension is then further concentrated and adjusted to pH 3,5 and filtered.

The solid can be subjected to the enzymatic hydrolysis as it is or it can be purified under heating in isopropilic alcohol, filtered and dried.

Yield: 55%

NMR (δ in DMSO-d6):
2,62 (6H, s, Ndimethyl); 3,40 (2H, t, etero Nmethylen); 3,50 (2H, q AB, 2CH₂); 3,65 (2H, s, CH₂—Ph); 3,76 (2H, s, CH₂—CO); 4,25 (2H, q AB,3CH₂); 4,65 (2H,m,CH₂-Ndimethyl); 5,05 (1H,d,6CH); 5,65 (1H,q,7CH); 6,92 (1H,s,thiazole 5H); 7,30 (5H,m,Ph).

C) Enzymatic Hydrolysis 10 g (15,5 mmoles) of the N-phenylacetyl protected cephalosporin obtained as per B) above are dispersed into 100 ml of H₂O at room temperature, and then taken back into solution with soda 1N at pH 7,5.

10 g of PG Amidase immobilized on Eupergit C (170 IU/g) are added to this solution following the enzymatic hydrolysis with NaCH1N by an automatic titrator.

The base consuming is noted to correspond to the formation of cefotiam (also followed in TLC). The enzyme is filtered when the reaction is ended and the solution is passed on an adsorbing resin XAD 1180.

The eluate of the resin which contains cefotiam is exsiccated, collected with HCl 4N and added with isopropanol to crystallize cefotiam dihydrochloride. Filtering and drying under vacuum are then effected.

Molar yield: 72%

EXAMPLE 4

PREPARATION OF CEFOTAXIME

A) preparation of the N-phenacetyl amino thiazol α methoxyimino acetic 10 g of methoxyiminoaminothiazolacetic acid in 100 ml of methylene chloride and 20 ml of triethylamine are added at 0° C. under stirring to 1,2 molar equivalents of the phenylacetic acid chloride. After some hours, 10 ml of triethylamine and further 0,5 equivalents of the chloride are further added. The reaction is complete after one night. The organic phase is washed with water, then dried and concentrated. The residual is slurried with a little of ethanol which removes an eventual residual of phenylacetic acid.

Yield: about 80%.

1H NMR DMSO-d6
3,75 (2H,s,PhCH₂); 3,90 (3H,s,NOCH₃); 7,30 (5H,m,Ph); 7,50 (1H,s,SCH); 12,75 (1H,s,COOH).

B) Preparation of the N-phenylacetylcefotaximina 2 g of the product obtained according to the Example 4-A in 60 ml of anhydrous THF are added at about 5° C. with 0,65 g of dicyclohesylcarboimide, corresponding to 0,5 molar equivalents. The mixture is kept under stirring at said temperature for 30 minutes, then for further 30 minutes at room temperature.

The precipitate of dicyclohesylurea formed in the midtime is filtered and the organic phase is cooled at −20° C.

A solution of 0,85 g of 7-ACA in 15 ml of methylene chloride and 2 ml of triethlylamine is added therewith in the space of some minutes. The temperature is then allowed to raise, so maintaining it for 3 hours. The solution is evaporated and then the residue is recovered with dioxane, said residue consisting of a mixture of N-phenacetylcefotaxime and of N-phenacetyl amino thiazol α-methoxyimino acetic thiazolacetic acid precipitating with diethylamine said last compound as a salt. Filtering drying are then effected. The residue is crystallized from ethyl acetate to give the desired N-phenacetylcefotaxime.

Alternatively, the separation can be effected digesting the residue consisting of the mixture of the two above mentioned compounds with a little of methylene chloride wherein the N-phenacetyl amino thiazol α-methoxy-imino acetic acid is less soluble, and then crystallizing the residue after evaporating CH2Cl2 from ethyl acetate.

Molar yield: 71%

1H-NMR DMSO-d6 2,05 (3H,s,COCH3); 3,55 (2H,qAB,2CH2); 3,75 (2H,s,PhCH2); 3,90 (3H,s,NOCH3); 4,65–5,0 (2H,qAB,3CH2); 5,18 (1H,d,6CH); 5,85 (1H,q,7CH); 7,3 (5H,m,Ph); 7,4 (1H,s,SCHC); 9,75 (1H,d,CONH); 12,8 (1H,S,COOH).

C) Enzymatic Hydrolysis 0,5 g of N-phenacetylcefotaxime are dissolved in 2 ml of acetonitrile and added, under stirring, to 25 ml of a buffer at pH 8.

About 400 UI of PGA on Eupergit C are added and the course of the hydrolysis is followed by TLC at 37° C. The reaction is ended in 40–50 minutes. Filtering and then concentrating in a very small volume are effected, acidifying at 0° C. Cefotaxime is recovered by filtration and is then re-dissolved after cooling with a little of ethyl acetate and filtered to remove the residue of the phenylacetic acid.

Molar yield: 65%

EXAMPLE 5

Carrying out the reaction as described in the Example 4, there has been found the possibility to produce other important cephalosporins, such as CEFTAZIDIME, CEFMENOXIME, CEFIXIME, CEFTRIAXONE, CEFODIZIME, CEFTIBUTEN, CEFTIZOXIME, CEFEPIME.

The 7-ACA amino thiazolyl protected adducts eventually 3-substituted from which the cephalosporins derive, where the amino protecting group is a phenyl acetyl group, taken into solution at pH 7,5, with or without CH3CN at 10%, have been subjected to the action of PGA whereas the pH has been maintained constant with a base. There has been demonstrated how, also in these cases, the PGA is selective, in its hydrolytic action, as to the 7-amidic bond of cephalosporin. At the end of the enzymatic hydrolysis, PGA is collected by filtration, concentrated under vacuum, slightly acidified and extracted with an organic solvent immiscible with water: the phenyl acetic acid. The aqueous phase is concentrated to a little volume and the above mentioned cephalosporins are recovered.

Obviously, in the case of some cephalosporins, the acetic moiety on the side chain had been previously protected as t-butylic ester to be then removed in the final step by slightly acidic hydrolysis.

The same procedure as disclosed for the N-protected phenylacetic series is valid for effecting the protection of phenoxy acetic moieties, in which case penicillin V amidase is used.

We claim:

1. A method for producing a 7-aminothiazolyl cephalosporanic compound of formula (I):

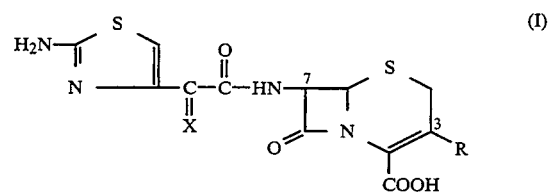

wherein R is selected from the group consisting of

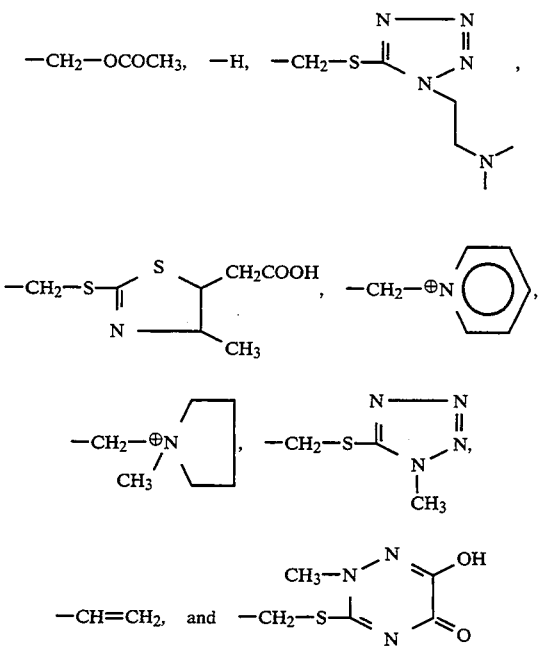

and X is selected from the group consisting of hydrogen, =N—O—CH3, =N—O—H, =N—O—CH2—COOH,

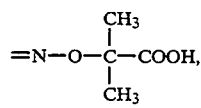

and —CH—CH2—COOH;

comprising reacting the 7-amino group of a compound of formula (II):

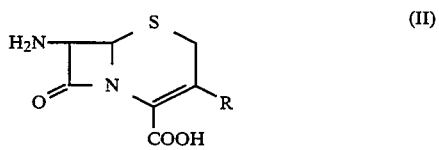

wherein R is defined as above, with the compound of formula (III):

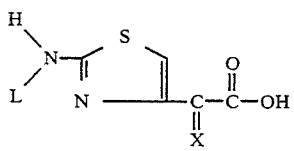

wherein L is a phenylacetyl or phenoxyacetyl group and X is defined as above, to form an N-protected aminothiazolyl cephalosporanic compound of formula (IV):

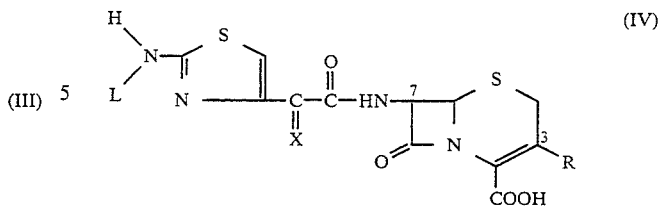

wherein R, L and X are defined as above;

hydrolysing said compound of formula (IV) with an enzyme selected from the group consisting of penicillin G amidase and penicillin V amidase in an aqueous solution at a temperature of from 0° C. to 50° C. at a pH from 5 to 9 to provide said compound of formula (I).

2. A method according to claim 1, characterized in that said hydrolysis is effected at a temperature of from 15° C. to 35° C. and at a pH from 6 to 8.

* * * * *